United States Patent [19]

Ginsburg et al.

[11] Patent Number: 4,769,005
[45] Date of Patent: Sep. 6, 1988

[54] SELECTIVE CATHETER GUIDE

[76] Inventors: Robert Ginsburg, 2489 Alpine Rd., Menlo Park, Calif. 94025; David F. Profitt, 1154 Madison, Santa Clara, Calif. 95050

[21] Appl. No.: 83,500
[22] Filed: Aug. 6, 1987
[51] Int. Cl.⁴ ........................................... A61M 25/00
[52] U.S. Cl. ..................... 604/53; 604/164; 604/256; 604/264
[58] Field of Search ............... 604/53, 280, 93, 164, 604/256, 264, 283; 128/657, 658

[56] References Cited

U.S. PATENT DOCUMENTS

| | | |
|---|---|---|
| 3,459,184 | 8/1969 | Ring . |
| 3,670,729 | 6/1972 | Bennett et al. . |
| 4,252,122 | 2/1981 | Halvorsen . |
| 4,306,562 | 12/1981 | Osborne . |
| 4,405,314 | 9/1983 | Cope . |
| 4,484,585 | 11/1984 | Baier . |
| 4,493,696 | 1/1985 | Uldall . |
| 4,568,329 | 2/1986 | Mahurkar ...................... 604/280 X |
| 4,586,926 | 5/1986 | Osborne . |
| 4,601,701 | 7/1986 | Mueller, Jr. . |

Primary Examiner—Stephen C. Pellegrino
Attorney, Agent, or Firm—Townsend & Townsend

[57] ABSTRACT

A guiding sheath for inserting guidewires or vascular catheters within a blood vessel includes an elongate body having plurality of axial lumens. At least some of the lumens project laterally from the body at preselected angles so that, when inserted therethrough, the guidewire or catheter will exit at said preselected angle to facilitate directing the guidewire or catheter to the proper location within the vascular system. Usually, the insertional sheath will include a primary axial lumen which is used for inserting the sheath on a guidewire to a location where a branching in the vascular system occurs. The sheath is then positioned under fluoroscopic guidance so that one of the lumens is then properly located to direct the guidewire or catheter in the desired direction.

14 Claims, 2 Drawing Sheets

U.S. Patent  Sep. 6, 1988  Sheet 1 of 2  4,769,005
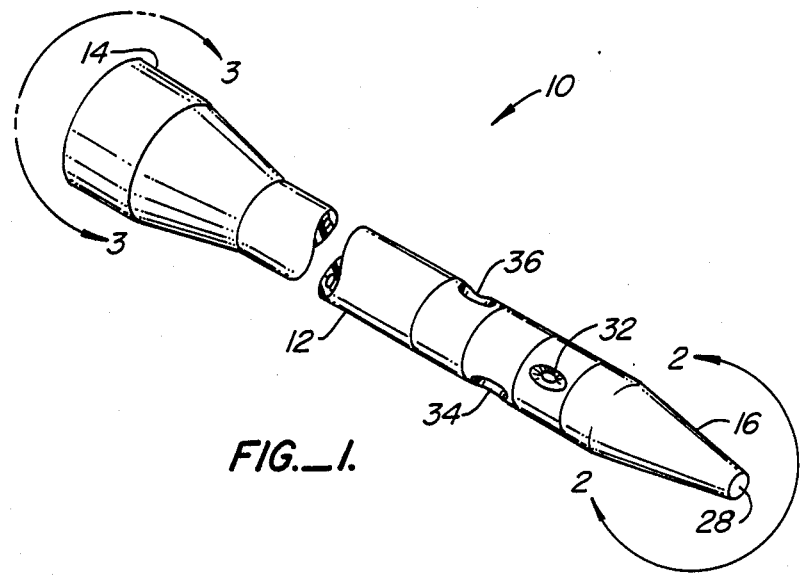
FIG._1.
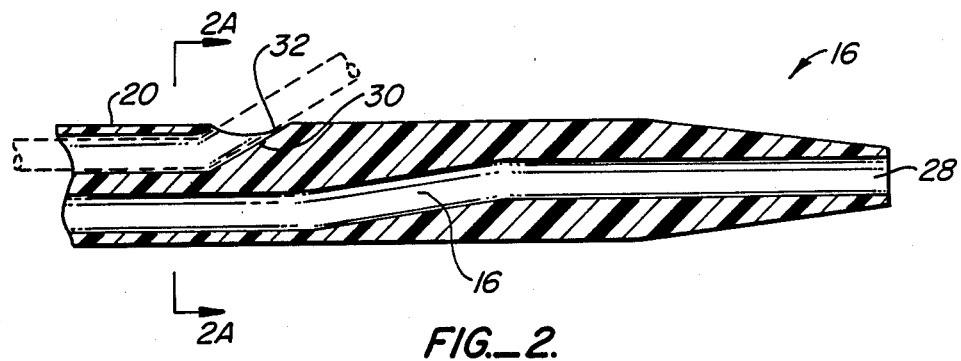
FIG._2.
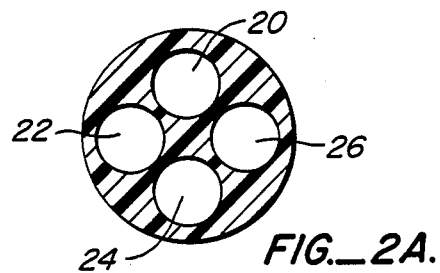
FIG._2A.

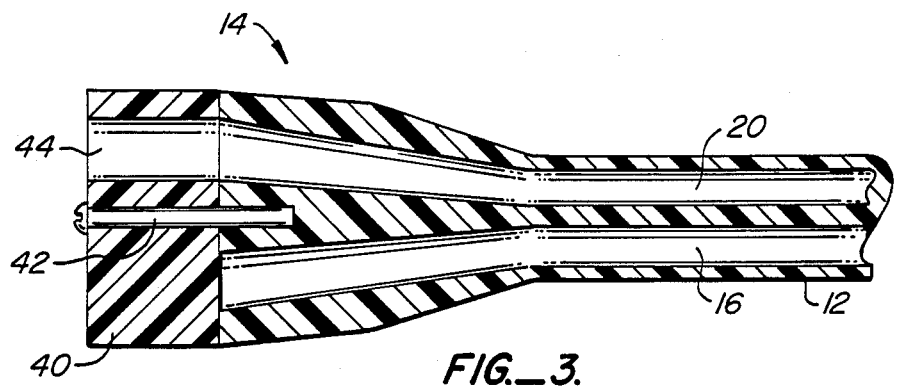
FIG._3.
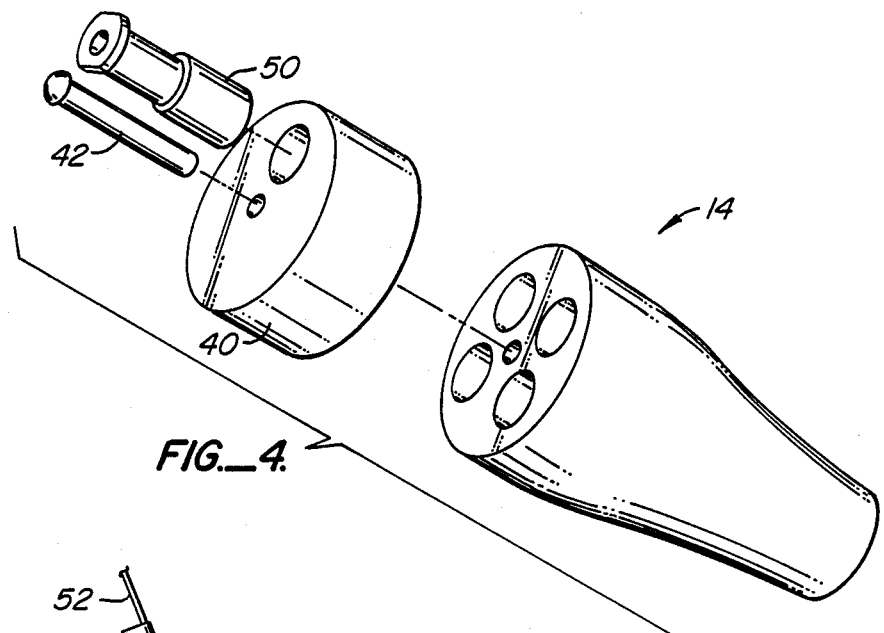
FIG._4.
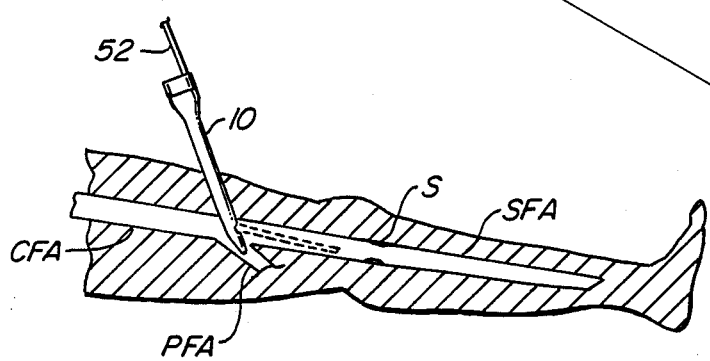
FIG._5.

SELECTIVE CATHETER GUIDE

BACKGROUND OF THE INVENTION

1. Field of the Invention

The present invention relates generally to apparatus and methods for inserting vascular catheters into blood vessels. More particularly, the invention relates to the construction and use of a guiding sheath for selectively directing such catheters into particular blood vessels.

A wide variety of non-invasive angioplastic methods exist for removing obstructions from blood vessels. Generally, these methods rely on the peripheral introduction of a catheter to the site of the obstruction and the manipulation of the catheter in some manner to remove the obstruction. The most common method employs a balloon-tipped catheter which is inflated at the site of the obstruction to dilate the passage therethrough. Also, laser catheters are used to ablate obstructions and certain catheters are then provided with cutting implements to excise the obstructions.

One difficulty with such angioplastic techniques has been the ability to properly locate the catheter within the patient's vascular system. In particular, difficulties arise whenever the arteries branch (bifurcate) and the catheter can proceed down the incorrect blood vessel.

Heretofore, catheters have generally been located by using a guidewire having a spring tip which is bent so that the direction of insertion can be selected by rotating the wire. The catheter is then inserted over the guidewire to the proper location. Alternatively, some catheters have an integral spring tip which is used to guide the catheter in an analgous manner.

The use of such guidewires and spring-tipped catheters, however, is not always satisfactory. In particular, placement of catheters into the superficial femoral artery (SFA) from the common femoral artery (CFA) has proved problematic. Because of the location of insertion and the angles at which the two arteries deviate, it can be very difficult to direct the guidewire into the superficial femoral artery.

For the above reasons, it would be highly desirable to provide apparatus and methods for the improved placement of catheters and guidewires within the vascular system. In particular, it would be desirable to provide an insertional sheath which can facilitate the directing of guidewires and spring-tipped catheters at branches within the vascular system, such as the bifurcation of the common femoral artery and the superficial femoral artery.

2. Description of the Background Art

U.S. Pat. Nos. 4,484,585 and 4,601,701 disclose catheters having multiple axial lumens with multiple lateral ports. Neither patent teaches the use of such a device as an insertion sheath. A double lumen cannula for hemodialysis is disclosed in U.S. Pat. No. 4,493,696. Insertional sheaths for catheters are described in U.S. Pat. Nos. 3,459,184 and 4,306,562. See also U.S. Pat. Nos. 3,670,729; 4,252,122; and 4,586,926 which relate to various insertional needles and catheter guides.

Dr. C. Cope of the University of Pennsylvania has developed an insertional catheter which provides for selective insertion of catheters into arteries. The insertional catheter is described in U.S. Pat. No. 4,405,314.

SUMMARY OF THE INVENTION

The present invention encompasses apparatus and methods for directionally inserting guidewires and catheters into blood vessels. The invention is particularly useful for selectively positioning the guidewire or catheter within the vascular system where it is oftentimes difficult to direct the guidewire or catheter down a desired branch. The invention is useful with both conventional guidewires and spring-tipped catheters, greatly facilitating their placement within the vascular system.

The apparatus of the present invention is an insertional sheath including an elongated body having a plurality of axial lumens therein. All of the lumens run from a proximate end of the body in the axial direction toward a distal end. At least some of the lumens, however, terminate at a point spaced inward from the distal end, where they project generally laterally from the body at a preselected angle. Usually, one of the lumens will extend axially the entire length of the sheath body and project through the distal tip in the axial direction. A sealing cap is provided at the proximal end of the body for closing off all of the lumens except one. Usually, the sealing cap will be rotatively mounted and include a single port which may be aligned with the various lumens to allow selection.

In use, the insertional sheath will be subcutaneously located to a desired location, usually using a conventional guidewire. The insertional sheath will be placed over the guidewire using the axial lumen which extends the entire length. After placement, the guidewire may be removed and a desired second guidewire or vascular catheter emplaced through one of the laterally deviating lumens. It will be appreciated that the insertional sheath may be first positioned by axial translation and rotation until one of the lumens is properly located to direct the guidewire or catheter down the desired branch of the vascular system. The guidewire or catheter is then inserted in through that lumen and located within the vascular system by conventional positioning techniques.

BRIEF DESCRIPTION OF THE DRAWINGS

FIG. 1 is an isometric view of the insertional sheath of the present invention.

FIG. 2 is a detailed, sectional view of the portion of the catheter indicated by line 2—2 of FIG. 1.

FIG. 3 is a detailed, sectional view of a portion of the catheter indicated by line 3—3 of FIG. 1.

FIG. 4 is a detailed, exploded view of the selected cap of the catheter.

FIG. 5 is a schematic view illustrating the placement of a vascular catheter in the superficial femoral artery using the insertional catheter of the present invention.

DESCRIPTION OF THE SPECIFIC EMBODIMENTS

Paragraph referring to FIG. 1, an insertional sheath 10 constructed in accordance with the principles of the present invention includes an elongate, generally rigid body 12 having a proximate end 14 and a distal end 16. The rigid body 12 is formed from a physiologically-acceptable material, usually a polymeric material, such as polyethylene. Conveniently, the rigid body 12 may be formed by conventional injection molding techniques.

The rigid body 12 of the insertional sheath 10 will generally be tapered at the distal end 16 and flared at the proximate end 14. The tapering of the distal end will facilitate subcutaneous insertion of the sheath 10, as described in more detail hereinafter. The length of the body 12 is not critical, and will depend on the particular location where the guidewire or catheter is intended to be inserted. Usually, the body 12 will have a length in the range from about 8 to 20 centimeters, more usually in the range of about 10 to 16 centimeters. The diameter of the sheath is also not critical and will depend on the number of internal lumens (as described hereinafter) as well as on the diameter of those lumens. Typically, the diameter of the body 12 will be in the range from about 5 to 10 French (Fr; 1 Fr equals 0.013 inches), usually being about 7.5 Fr.

Referring now also to FIGS. 2, 2A, and 3, the body 12 of sheath 10 includes four axial lumens 20, 22, 24, and 26 extending from the proximate end 14 toward the distal end 16. As best observed in FIG. 2A, the lumens 20-26 will generally have circular peripheries and be evenly spaced apart across the cross section of the body 12. Lumen 24 extends the entire distance from proximate end 14 to the distal end 16, as best observed in FIG. 2. Lumen 24 terminates in port 28 at the tip of distal end 16. The remaining lumens 20, 22, and 26, terminate at points spaced away from the distal end 16. As in FIG. 2, lumen 20 deviates laterally in a short section 30 and is open to the exterior of the sheath 10 through a port 32. Similarly, lumen 22 terminates in a port 34 (FIG. 1) and lumen 26 terminates in a port 36. The ports 32, 34, and 36 are axially spaced-apart along the body 12 of sheath 10 and, optionally, may project outward from the body at differing angles. Usually, the angle of lateral deviation of the port from the lumen will vary in the range from about 5° to 65° degrees, more usually in the range from 30° to 95° degrees. By employing ports having different exit angles from the associated lumens, different angles may be selected for inserting the guidewire or catheter after the sheath 10 has been located within the patient. It will be appreciated that it is not always possible to accurately position the sheath when it is initially put in place so that the ability to select among different exit angles would be a benefit.

Referring now in particular to FIG. 3, a seal cap 40 is rotatably mounted at the proximate end 14 of body 12 on an attachment pin 42. The seal cap 40 includes a single port 44 which is positioned so that it may be aligned with any of the lumens 20-26 by properly rotating the cap 40. When aligned with one lumen, the cap seals the remaining lumens to prevent blood loss and contamination through said remaining ports.

Frequently, a luer fitting 50 (FIG. 4) may be employed for inserting the guidewire or catheter within the lumen.

In an alternate embodiment of the present invention (not illustrated), the exit ports 32, 34, and 36 may be axially aligned along the exterior of the sheath 10 so that guidewires and catheters will exit from the same axial position along the sheath from each of the lumens. The angle of exit from the various lumens, however, may differ allowing the surgeon to select which angle of deviation is to be used.

Referring now to FIG. 5, the use of the sheath 10 of the present invention for inserting a flexible catheter 52 into the superficial femoral artery (SFA) will be described. Usually, a first guidewire (not illustrated) is inserted into the common femoral artery (CFA) by conventional techniques. The sheath 10 is then inserted into the common femoral artery CFA by passing the sheath over the guidewire which passes through the primary axial lumen 24. The sheath may be generally located using radial opaque markers 54 (FIG. 1) which are located adjacent the lateral exit ports 32-36. Once the sheath is generally located, the first guidewire will be removed. After such removal, the sealing cap 40 will be rotated to close off the primary lumen 24.

By observing the procedure through a fluoroscope, it is possible to select which of the lumens appear best positioned for inserting the guidewire and/or vascular catheter. The exit port cf that lumen can be further positioned by rotating and axially translating the sheath until the location has been optimized. At that point, the sealing cap 40 will be rotated and the guidewire or catheter inserted through the selected lumen until it exits from the side port. By observing the procedure fluoroscopically, the entry of the guidewire into the superficial femoral artery (SFA) can be observed. Prior to use of the sheath 10 of the present invention, it was often a problem preventing the guidewire or catheter from entering the peripheral femoral artery (PFA) which joins the superficial femoral artery (SFA) at the branching from the common femoral artery (CFA).

Once the guidewire or catheter 52 is directed down the superficial femoral artery (SFA), the positioning at the region of stenosis can be accomplished by conventional techniques. It will be appreciated that if a guidewire is being used, the guidewire will be brought to the region of stenosis and a catheter inserted in over the guidewire to said region. Alternatively, if a self-guiding spring-tipped catheter is being used, it may be guided to the proper region without the use of a guidewire.

Although the foregoing invention has been described in some detail by way of illustration and example for purposes of clarity of understanding, it will be obvious that certain changes and modifications may be practiced within the scope of the appended claims.

What is claimed is:

1. A sheath for directionally inserting a guidewire or catheter into a blood vessel, said sheath comprising:
 an elongate body having a proximate end and a distal end, said body including at least two lumens disposed generally axially therein, where (1) a first of the lumens extends from the proximate end to the distal end and projects axially from the distal end and (2) a second of the lumens extends from the proximate end to a first point between the proximate end and the distal end and projects generally laterally from the body at a first preselected angle relative to the axial direction; and
 means at the proximate end of the body for selectively passing the catheter or guidewire through one of the lumens while sealing the other lumen or lumens.

2. A sheath as in claim 1 wherein said body further includes a third lumen which extends to a point between the proximate end and the distal end and projects laterally from the body at a second preselected angle relative to the axial direction.

3. A sheath as in claim 2, wherein the first point and second point are axially spaced-apart.

4. A sheath as in claim 2 wherein the first point and second point are at substantially the same axial position on the body, but project in different lateral directions.

5. A sheath as in claim 1, wherein the means for selectively passing a catheter includes a cap attached to rotate about a substantial axial axis at the proximate of the body, said cap including a single port which selectively aligns with the lumens to allow insertion of the catheter or guidewire while sealing the remaining lumen or lumens.

6. A sheath for directionally inserting a catheter or guidewire into a blood vessel, said sheath comprising:
 an elongate cylindrical body having a flared proximate end and a tapered distal end defining a tip, said body having (1) a first lumen extending from the flared proximate end to the proximate end of the tip of the distal end where said first lumen projects from said tip in a substantially axial direction, and (2) a second lumen extending from said flared proximate end to a first point between the proximate end and the distal end where said second lumen projects laterally through the cylindrical wall at a first preselected angle relative to the axial direction; and
 a cap rotatably secured to the flared distal end of the body, said cap including a single port which selectively aligns with one lumen at a time to allow insertion of the catheter or guidewire through the aligned lumen while the remaining lumens remain closed.

7. A sheath as in claim 6, wherein said elongate body includes a third lumen extending from said flared proximate end to a second point between the proximate end and the distal end where said second lumen projects laterally through the cylindrical wall at a second preselected angle relative to the axial direction.

8. A sheath as in claim 7, wherein the first and second points are axially-spaced apart on the elongate cylindrical body.

9. A sheath as in claim 7, wherein the first and second preselected angles are the same.

10. An improved insertion sheath of the type including an elongate body having an axial lumen for inserting a vascular catheter or guidewire, said improvement comprising at least one additional axial lumen, which additional lumen extends from a proximate end of the body and projects generally laterally from the body at a preselected angle relative to the axial direction by the body, and means at the proximate end for selectively passing the catheter or guidewire through one of the lumens while sealing the other lumen or lumens.

11. A method for inserting a vascular catheter or guidewire into a blood vessel, said method comprising:
 subcutaneously inserting a guide sheath proximate the blood vessel, said guide sheath having an elongate body with a plurality of lumens extending from one end and defining lateral discharge ports which are axially-spaced apart along the body;
 positioning the sheath so that the discharge port of one of said lumens is generally aligned with the blood vessel; and
 inserting the vascular catheter or guidewire through said one lumen, whereby the catheter or guidewire enters the blood vessel.

12. A method as in claim 11, wherein the guide sheath is positioned on a guidewire which runs through a lumen extending axially from one end of the elongate body to the other end.

13. A method as in claim 11, wherein the sheath is positioned by rotating.

14. A method as in claim 11, wherein the sheath is positioned by axial translation.

* * * * *